United States Patent [19]
Murphy et al.

[11] Patent Number: 5,992,242
[45] Date of Patent: Nov. 30, 1999

[54] SILICON WAFER OR DIE STRENGTH TEST FIXTURE USING HIGH PRESSURE FLUID

[75] Inventors: Adrian Murphy; Manickam Thavarajah, both of San Jose, Calif.

[73] Assignee: LSI Logic Corporation, Milpitas, Calif.

[21] Appl. No.: 09/072,915

[22] Filed: May 4, 1998

[51] Int. Cl.$^6$ ................................................. G01N 3/00
[52] U.S. Cl. ................................................. 73/840
[58] Field of Search .......................... 73/837, 838, 840, 73/849, 851, 816, 812

[56] References Cited

U.S. PATENT DOCUMENTS

| | | | |
|---|---|---|---|
| 4,755,746 | 7/1988 | Mallory et al. | 324/158 F |
| 4,820,976 | 4/1989 | Brown | 324/158 F |
| 4,967,602 | 11/1990 | Norton | 73/840 |
| 5,034,685 | 7/1991 | Leedy | 324/158 F |
| 5,070,297 | 12/1991 | Kwon et al. | 324/158 P |
| 5,313,157 | 5/1994 | Pasiecnik | 324/158 P |
| 5,424,634 | 6/1995 | Goldfarb et al. | 73/838 |
| 5,424,988 | 6/1995 | McClure et al. | 365/201 |
| 5,557,573 | 9/1996 | McClure | 365/201 |
| 5,670,888 | 9/1997 | Cheng | 324/754 |

OTHER PUBLICATIONS

Field et al., "An improved strength–measurement technique for brittle materials" J. Phys. E: Sci. Instrum., vol. 13, No. 3 (Mar. 1980).

Primary Examiner—Robert Raevis

[57] ABSTRACT

An Integrated Circuit (IC) wafer test fixture includes a baseplate and a top plate. During testing, an IC wafer is positioned between the baseplate and top plate with annular rubber gaskets, forming sealed cavities above and below the IC wafer. A fluid pressure generator with a pressure gauge inserts a fluid under pressure into one of the cavities, causing the IC wafer to be subject to stress. The fluid distributes a uniform pressure load on the surface of the IC wafer. The pressure of the fluid may be gradually increased until a desired pressure is obtained or the wafer fails. The pressure at failure is recorded, and by calculation the failure stress of the IC wafer can be determined. A second embodiment of the test fixture includes a pressure vessel with a threaded sealed opening at the top and a stepped sealed opening at the bottom. The inner diameter of the insert is sized for an IC wafer. In use, the IC wafer is positioned on top of the insert, and the pressure vessel is sealed. A fluid pressure generator with a pressure gauge injects fluid under a controlled pressure within the sealed pressure chamber, stressing the IC wafer, as a uniform pressure load is distributed over the surface of the IC wafer. The pressure recorded, and by calculation the stress of the IC wafer may be determined.

1 Claim, 2 Drawing Sheets

SILICON WAFER OR DIE STRENGTH TEST FIXTURE USING HIGH PRESSURE FLUID

BACKGROUND OF THE INVENTION

The present invention relates to testing of a wafer used in the fabrication of integrated circuit (IC) dies, and more particularly to testing the wafer in a test fixture using a high pressure fluid.

In the last few decades, the electronics industry has literally transformed the world. Electronic products are used by, or affect the daily lives of, a large segment of the world's population. For example, telephones, television, radios, Personal Computers (PCs), laptop PCs, palmtop PCs, PCs with built-in portable phones, cellular phones, wireless phones, pagers, modems, and video camcorders, are just a few of the electronic products that have been developed in recent years and which have been made smaller and more compact, while providing more and/or enhanced functions than ever before. The integrated circuit (IC) die or IC chip, and the more efficient packaging of the IC die, have played a key role in the success of these products.

There are three distinct stages in the manufacture of an IC die. The first stage is the material preparation. In this stage, the raw materials are mined and purified to meet semiconductor standards. The second stage consists of forming the material into wafers. The diameters of the wafers can vary between 1 and 12 inches. In the third stage, wafer fabrication, the IC dies are formed in and on the wafer. Up to several thousand IC dies can be formed on a wafer but 200 to 300 are more common.

After wafer fabrication is completed, the wafer with the IC dies is mechanically tested to determine if the wafer and IC dies will survive the stresses imposed by final assembly and testing. Also, the tests determine the maximum stress the wafer and IC dies can withstand before the onset of cracking. These tests can act as a guide in the construction of a new IC package.

FIGS. 1a & 1b show the present method of testing. FIG. 1a illustrates a typical three point test setup and FIG. 1b shows a four point test setup. Both of these tests are known in the art. The test piece, which in this case is a silicon wafer 100, is simply supported on two edges by supports 110. These supports prevent the transverse displacement of the edge of the wafer 100 and are made of strong material, such as metal. At the center of the wafer 100, a load 120 (for three point) or a load 130 (for four point) is applied. The load 120 is a single point load and the load 130 uses two points, both of which are applied gradually to the wafer 100. As the load 120 or 130 is applied downwardly, the wafer 100 starts to flex along its length and measurements are made of the load the wafer 100.

The problem associated with the methods of testing shown in FIGS. 1a & 1b is that, as the load 120 or 130 is applied to the wafer 100, there are high stress concentrations at the point where the supports 110 touch the wafer 100 and also at the point where the load 120 or 130 touch the wafer 100. Unfortunately, silicon is a brittle material and is subject to localized cracking or micro-cracking at the point where the test load 120 or 130 is applied and also at the point where the wafer 100 contacts the support members 110. These point load areas generate high local stresses which are the starting point for cracking or micro-cracking. The resultant micro-cracking may influence the test results in uncontrolled ways, thus giving highly variable results. Moreover, the method of testing wafers shown in FIGS. 1a & 1b is not representative of actual loads that an IC die may experience in use because the test only applies point loads on discrete portions of the wafer 100 and does not mechanically test the rest of the wafer 100 or IC dies. In addition, when the wafers are very thin, the weight of the test device (FIGS.s 1a and 1b) may interfere with the test and compromise the results. Removing this inaccuracy by mechanical balancing may be very difficult to achieve, if at all.

Thus, when wafers are currently tested using the methods illustrated in FIGS. 1a & 1b, the contact between the test apparatus and the wafer is an area of high stress concentration and is the starting point of cracking or micro-cracking of the wafer. Disadvantageously, this means that a wafer that might have been good is damaged because of the test fixture and method of testing. As a result, many parts may be disposed of that might otherwise have been good, thus increasing costs.

In current manufacturing practice, the wafers are not mechanically tested for strength.

In view of the above, it is evident that what is needed is an apparatus and method of wafer testing to determine their suitability for use in a high stress package (i.e., flip-chip). The testing can be done prior to die fabrication to determine the base silicone wafers suitability for use in flip-chip or high stress packaging, and post die fabrication to insure the processing was not detrimental to the wafer's original strength. The testing should provide a uniform load distributed over the surface of the wafer, can be used when the IC dies are on the wafer without damaging them, and can be used with many size wafers or components, thereby making the testing more realistic and cost effective.

SUMMARY OF THE INVENTION

The present invention allows the manufacturer to test the wafer in a manner that does not induce point loads with high stress concentrations on the wafer. Advantageously, the present invention reduces the amount of damage to the wafer from the test apparatus, allowing the manufacturer to test with more confidence in the test method and make the testing more cost effective.

While traditional testing uses point loads with high stress concentration areas, the present invention applies a continuous load over the entire surface of the wafer. This method of testing more closely emulates the way a load is actually applied in an assembled IC package, thus the resultant stress and strain applied by the test is more realistic and hence more meaningful.

In a first embodiment of the invention, the wafer is placed in a test fixture between a base plate and an annular top. Between the wafer and the base plate is a first compliant annular gasket that supports the wafer around its perimeter during testing. The inner diameter of the first compliant gasket forms a lower cavity between the base plate and the wafer. On top of the wafer is a second compliant gasket that is placed between the wafer and the annular top. The second gasket supports the wafer around its perimeter during testing. The inner diameter of the second gasket forms an upper cavity between the annular top and the wafer. In the center of the base plate is a fluid inlet that allows high pressure fluid (e.g. nitrogen, air, oil, water or de-ionized (DI) water) to enter the lower cavity. The choice of fluid is dependent on different factors of the test. For example, if the wafer testing is to be done in a fabrication facility (clean area), then the choice would be a clean fluid such as clean dry air (CDA), nitrogen (N2) or de-ionized water (DI water) to prevent contamination of the facility and tooling.

During testing, the test fixture is located in a press so that the press exerts a clamping force on the test fixture to hold the wafer firmly in place between the baseplate and annular top and thus prevents the test fixture from separating during the test. A high pressure fluid is introduced through a valve into the lower cavity by means of a pressure generator. The fluid applies a distributed load over the surface of the wafer, and the fluid pressure is measured by a gauge or recorder. As the pressure rises in the cavity, stress induced in the wafer will eventually cause the wafer to fracture and fail. The failing wafer will rupture, relieving the pressure from the lower cavity into the upper cavity. By accurately recording the rupture pressure, the applied load can be determined. Further, by calculation, the failure stress in the wafer or die can be determined. Optionally, the pressure may be measured by electronic means and the information sent to a recording instrument, such as a computer. It is also possible to measure wafer deflection by non-contact methods during the test, enhancing any further calculations required or performed.

In a second embodiment, the wafer is placed inside a pressure vessel. The pressure vessel has an opening at the top and the bottom. A threaded cap is used to seal the top opening while an interchangeable insert is used to seal the bottom opening. The interchangeable insert is annular in shape having an opening in the center. The opening of the insert is surrounded by an O-ring. The O-ring supports the wafer during testing and seals the opening, preventing the high pressure fluid from escaping around the wafer and out the opening. Once the insert, wafer and cap are in place, the interior of the pressure vessel forms a pressure chamber. A fluid inlet is located in the wall of the pressure vessel and allows the high pressure fluid from the pressure generator to enter the pressure chamber. The fluid applies a distributed load over the surface of the wafer and the fluid pressure is measured by a gauge or recorder. As the pressure rises in the pressure chamber, stress induced in the wafer will eventually cause the wafer to fracture and fail. The failing wafer will rupture, relieving the pressure from the pressure chamber through the opening in the insert. By accurately recording the rupture pressure, the applied load can be determined and by calculation, the failure stress in the wafer or die can be determined.

It is thus a feature of the present invention to allow wafers and IC dies to be tested in a more realistic environment by distributing a load uniformly on the surface of the wafer, while eliminating high stress concentrations due to point loads.

BRIEF DESCRIPTION OF THE DRAWINGS

The above and other aspects, features and advantages of the present invention will be more apparent from the following more particular description thereof, presented in conjunction with the following drawings wherein.

Below is a list of reference numbers associated with the figures.

| No. | Component |
|-----|-----------|
| 10 | Test Fixture |
| 15 | Wafer |
| 20 | Baseplate |
| 25 | Surface |
| 30 | Gasket |
| 35 | Lower Cavity |
| 40 | Fluid Inlet |
| 45 | Top |
| 50 | Upper Cavity |
| 55 | Surface |
| 60 | Gasket |
| 65 | Pressure Generator |
| 70 | Valve |
| 75 | Gauge or Recorder |
| 80 | Computer Link |
| 85 | Press |
| 90 | Exhaust Port |
| 95 | Fluid Reservoir |
| 100 | Wafer |
| 110 | Supports (prior art) |
| 120 | 3 Point Load |
| 130 | 4 Point Load |
| 200 | Test Fixture |
| 210 | Pressure Vessel |
| 220 | Upper Cap |
| 230 | Interchangeable Insert |
| 240 | Pressure Chamber |
| 250 | Fluid Inlet |
| 260 | Gasket |
| 270 | First O-ring |
| 280 | Lower Step Surface |
| 290 | Second O-ring |
| 300 | Top Surface of the Insert |
| 310 | Opening in the Insert |

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
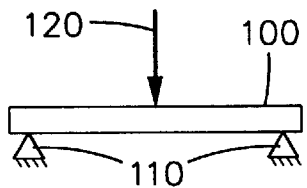
FIG. 1a is a schematic diagram of a three point test in accordance with the prior art.
Figure 1B:
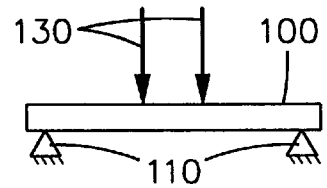
FIG. 1b is a schematic diagram of a four point test in accordance with the prior art.

FIGS. 1a & 1b illustrate prior art test fixtures and are described in the "Background of the Invention" portion of this application.

The present invention may be used to test the wafer during different stages of wafer fabrication. The first is to conduct pre-tests on wafers to determine their suitability for specific applications, i.e., assembly into packages that induce high stresses in the silicone wafer material. The testing of the invention may also be done on integrated circuit wafers, individual dies or even die(s) assembled into packages. When testing is done in the fabrication area (clean area), cleanliness is paramount and any methods and materials used must be such that they do not contaminate the tools, chemicals or fabrication area. To this end, materials used in the test fixture such as metals, gaskets and sealant compounds must be compatible with the fabrication process. Outside the fabrication area, other materials could be used so long as there is no further processing required of the wafer, die or assembly.

It is not necessary to destroy the wafer or die during testing to evaluate its strength or elastic properties. While testing to failure does test the ultimate strength, it is possible (in accordance with the present invention) by combining the degree of deflection of the wafer during the test against a known applied load, to determine the elasticity characteristics of the wafer. Advantageously, when the applied load does not reach the level to cause failure, the process can be applied to every wafer. Thus, there need be no loss of wafers during testing (i.e., no destructive testing), thereby lowering the cost. One of the best methods of measuring wafer defection is to use a non-contact deflection measuring device that does not interfere with the test in progress and that does not touch the wafer (which might cause damage).

Figure 2:
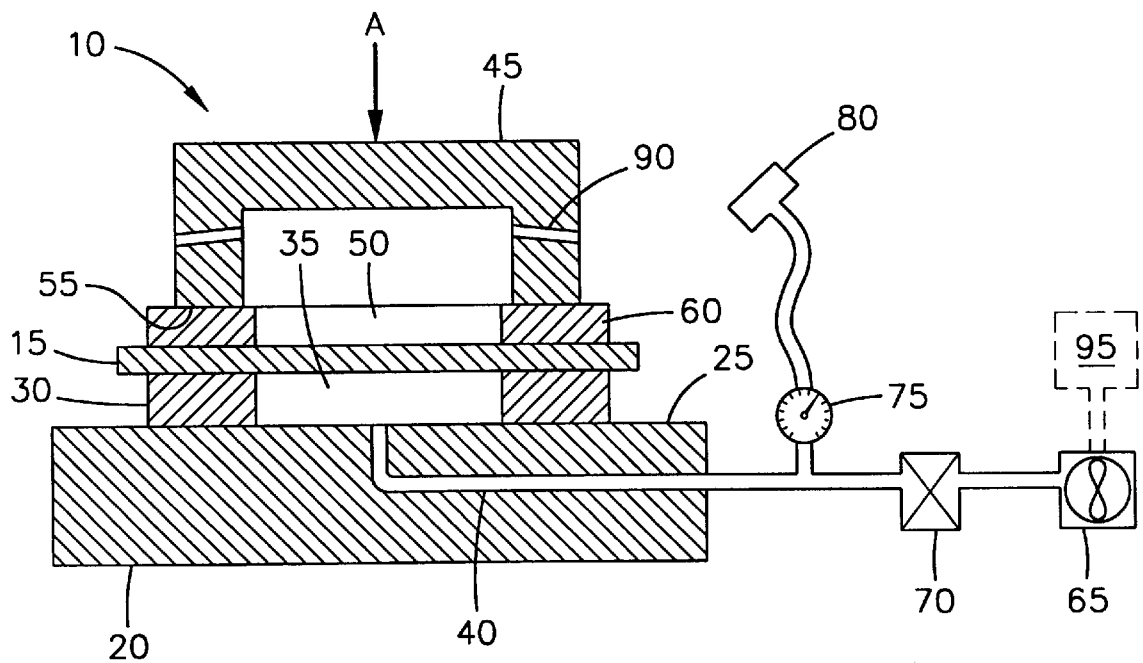
FIG. 2 is a cross-sectional view of a wafer test fixture made in accordance with the present invention.

FIG. 2 shows one embodiment of the present invention utilizing a wafer test fixture 10. The fixture 10 differs from the prior art fixtures in that the load applied to the wafer or IC die is uniformly distributed over the surface of the wafer and is not a point load. Spreading the load over the entire surface of the wafer advantageously eliminates the local effects of stress concentrations due to point loads. This is true even if the surface undulates, as is the case on the active surface of an IC. An important feature of the invention is that the test load is applied through a medium of fluid rather than via a discrete contact point.

A silicone wafer 15 (or IC die) is inserted between an upper portion and lower portion of the test fixture 10. The lower portion of the test fixture 10 comprises a base plate 20 with a compliant gasket 30. The baseplate 20 has a upper surface 25 with a roughness of less than about $4\mu$ inch (4 microinches) and a flatness of less than about 0.001 inch. The baseplate 20 should be made from metal, such as steel, aluminum or other suitable material (even some plastics). Between the base plate 20 and the wafer 15 is the compliant annular gasket 30. The gasket 30 is made of compliant material such as rubber, cork, or any other suitable material that can be used for support and sealing. The gaskets serve two purposes. First they provide a compliant surface for the wafer to rest upon. The more compliant the surface, the less likely the wafer or die is to localized stress and, thus, to false readings and/or stress cracking. Second, the gaskets keep the pressurized fluid in the cavity, which confines the pressure build up to the space within the cavity. [Note: the term "fluid" is used herein inots broad scientific context to denote either a gas or a liquid.] The choice of gasket material is dependent on the testing to be performed. For example, if the testing is done in a fabrication facility (clean area), then cork should not be used since it is considered "dirty" and is also brittle. If the tests are performed on "live" dies in a fabrication area in a non-destructive test, the gasket material should be static charge dissipative, i.e., the gasket should be made from dissipative rubber or soft polymer. Additionally, it is not essential that the gasket material provide a perfect fit, so long as the leak rate is less that the inflow rate such that pressure can be built up for testing. With this type of testing, a clean fluid such as CDA or N2 would be used so if it leaks, the escaping gas is not a problem. On the other hand, if the testing of the wafer is to be destructive (i.e., find the maximum pressure of the wafer), a liquid (DI water) is best as liquids do not "explode" as gases do. Another reason for the gasket material is to cushion the brittle wafer material from the metal of the test fixture so that the test fixture does not cause any micro-cracks in the wafer as is common with the current 3- and 4-point test fixtures as the type shown in FIGS. 1a and 1b.

The gasket 30 has an inner diameter that is dimensioned to support the edges of the wafer 15 during testing and a thickness that will form a lower cavity 35 when the wafer 15 is placed on the gasket 30. The lower cavity 35 must be large enough so as not to interfere with any components that are located on the wafer 15, e.g., IC dies, wire tabs, etc. A fluid inlet 40 is located in the baseplate 20. The fluid inlet 40 opens into the lower cavity 35, supplying a high pressure fluid for testing and connecting to other equipment, as described below.

The upper portion of the test fixture 10 comprises an annular top 45 with a gasket 60. A lower surface 55 of the top 45 has a surface roughness of less than about $4\mu$ inch and a flatness less than about 0.001 inch. Positioned between the top 45 and the wafer 15 is another compliant gasket 60. The gasket 60 is made of compliant material such as rubber, cork, or any other suitable material that can be used for support and sealing. The gasket 60 is annular is shape with an inner diameter that is sized to support the circumference of the wafer 15 during testing. The top 45 and the gasket 60 form an upper cavity 50 that is sized such that it does not interfere with any structure on the wafer surface during testing, e.g., IC dies, wire tabs, etc. The inner diameter of the gaskets 30 and 60 may also have different shapes, for example if the wafer 15 has been cut in a square or oval pattern, the gaskets 30 and 60 would be shaped and sized to fit such a pattern. Sealant grease, such as grease sold by VAT Inc. part number N-6951012, may also be used on the gaskets to assist in sealing the components during testing, as desired.

The fluid inlet 40 is connected to a pressure generator 65. The pressure generator 65 may use different types of high pressure fluids for testing, such as air, water or oil. The pressure generator 65 may contain the fluid internally or may be attached to a fluid reservoir 95 (as shown in FIG. 2). The fluid flow is controlled by a micro-metering valve 70. There is also a gauge or recorder 75 that measures the pressure during testing. The recorder 75 may also be optionally linked via a cable 80 to a computer for analysis.

Figure 3:
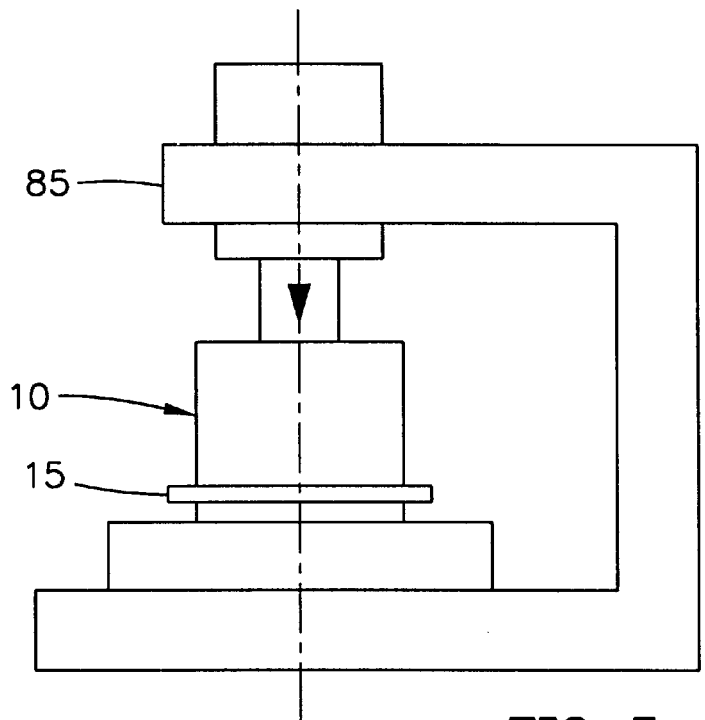
FIG. 3 is a schematic diagram of the wafer test fixture held in a press.

In use, the wafer 15 is inserted into the test fixture 10 between the lower gasket 30 and the upper gasket 60. The test fixture 10 is then inserted into a press 85, shown in FIG. 3. Many different types of presses may be used, e.g. hydraulic, air, screw, etc. Once the test fixture 10, with the wafer 15 and gaskets 30 and 60 placed therein, is put into the press 85, the press 85 puts a clamping load (in the direction of arrow A) on the test fixture 10 stack, holding the wafer 15 firmly in place.

Once the test fixture 10 is secured in the press 85, a fluid is chosen (e.g. nitrogen, air, oil, water or de-ionized (DI) water) for use with the test fixture. The choice of fluid is dependent on different factors of the test. For example, if the wafer testing is to be done in a fabrication facility (clean area), then the choice would be a clean fluid such as clean dry air (CDA), nitrogen (N2) or de-ionized water (DI water) to prevent contamination of the facility and tooling. The pressure generator 65 introduces the chosen high pressure fluid slowly into the lower cavity 35 via the fluid inlet 40. The fluid flow is controlled by the valve 70. The fluid flows into the cavity 35 and pressurizes the lower cavity 35 between the baseplate 20 and the wafer 15 with the gasket 30 sealing the fluid in the cavity 35. The fluid applies a continuous and uniform load on the wafer 15. The fluid pressure is measured by the gauge or recorder 75. Deflection of the wafer may be sensed and measured simultaneously throughout the test by optical sensors mounted adjacent to the wafer or die surface. As the pressure rises in the cavity 35, stress induced in the wafer 15 will eventually cause the wafer to fracture and fail. The failing wafer 15 will rupture, relieving the pressure in the lower cavity 35 into the upper cavity 50. The upper cavity 50 is closed so that silicon particles from the wafer 15 remain within the test fixture 10 and do not pose a hazard for the operators. Noise from the rupture of the wafer 15 and the release of pressure will also be reduced. Optionally, the upper cavity 50 may have exhaust ports 90 (FIG. 2) to further relieve the pressure.

By accurately recording the pressure at rupture, the failure pressure or load is determined. Also by calculation, the ultimate stress in the wafer 15 or IC die can be determined. The relationship between the load and stress can be found in engineering books such as "Marks' Standard Handbook for Mechanical Engineers". There are a number of different formulas, depending on the clamping method and other dimensional factors. For example, the formula used for calculating the stress for a uniformly distributed load is:

$$\sigma = k(\omega r^2/t^2)$$

Where σ=calculated stress, k=coefficient obtained from standard tables (in the case of a circular plate such as the wafer, k=1.24), ω=measured uniformly distributed load, r=radius of wafer and t=wafer thickness. Optionally, the pressure may be measured electronically and the information sent via a computer link 80 to a recording instrument or computer-based analytical device.

Figure 4:
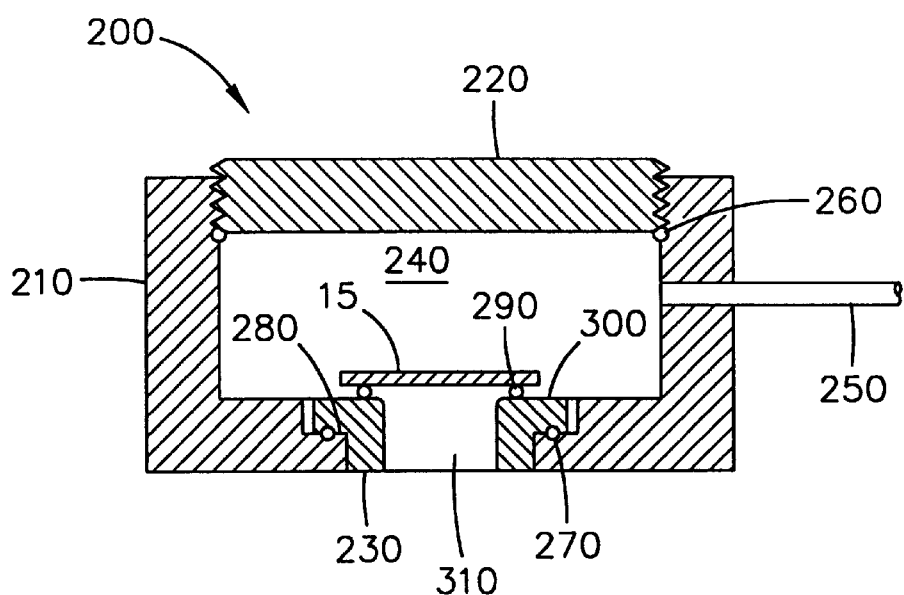
FIG. 4 is an alternate embodiment of the wafer test fixture.

FIG. 4 shows an alternative embodiment of the present invention. The test fixture 200 consists of a pressure vessel 210 including an upper cap 220 and an interchangeable insert 230 forming a pressure chamber 240. The pressure vessel 210 shown in FIG. 4 is made of metal and is cylindrical in shape, with a threaded opening at the top and a stepped opening at the bottom. The cap 220 is generally circular in shape with threaded circumference. The thread of the cap 220 matches the thread of the pressure vessel 210 such that a pressure seal is formed when the cap 220 is screwed on the pressure vessel 210. To assist in sealing the threads, sealing grease or a gasket 260 may be used. The interchangeable insert 230 is annular in shape with the outer diameter stepped to match the lower opening of the pressure vessel 210 and the inner diameter sized to match the wafer 15 being tested. A first O-ring 270 or sealing grease may be used on the lower step surface 280 to assist in pressure sealing between the pressure vessel 210 and the insert 230. A second O-ring 290 is located on the upper surface 300 of the insert 230. The O-ring 290 supports the wafer 15 and seals the opening of the insert 230 during testing. Optionally, sealing grease may be used in place of the O-ring 290. On the side of the pressure vessel 210 is a fluid inlet 250. The fluid inlet 250 is connected to the pressure generator 65, as described above.

In use, an insert 230 is selected that matches the wafer 15 size to be tested. The insert 230, with a wafer 15 mounted thereon via O-ring 290, or equivalent, is placed in the lower opening of the pressure vessel 210. The cap 220 is then screwed on the pressure vessel 210 to seal the opening. The pressure generator 65 introduces high pressure fluid slowly into the pressure chamber 240 via the fluid inlet 250, thereby applying a pressure force uniformly over the upper surface of the wafer 15. As the pressure increases, the insert 230 is pressed against the O-ring 270 and the wafer 15 is pressed against the O-ring 290, further sealing the pressure chamber 240. The pressure force required to test the wafer will vary depending on the type of testing to be done (destructive vs non-destructive), clamping method used, the diameter of the opening (310), the thickness of the die or wafer, the processing that the wafer or die has experienced and the manufacturer of the wafer. Depending on these factors, the pressure could be as little as 10 psi to as much as 3000 psi. The fluid pressure is measured by a gauge or recorder 75, as described previously in connection with FIG. 2. As the pressure rises in the pressure chamber 240, the wafer 15 deflects and stress induced, and by calculation, the stress in the wafer 15 or die can be determined. For non-destructive testing, a precalculated pressure is applied for testing the wafer 15 to determine acceptability. If destructive testing of the wafer 15 is desired, the pressure is increased until the wafer ruptures, relieving the pressure through the opening 310 in the insert 230 and by accurately recording the pressure at rupture, the ultimate load of the wafer 15 can be determined.

As evident from the above description, the present invention allows wafers, IC dies and even assembled IC packages to be tested in a more realistic environment and eliminates high stress concentrations due to test-fixture-induced point loads. These tests may also be used as a screening test (i.e., non-destructive) for the wafer, IC die or assembled IC package.

While the invention herein disclosed has been described by means of specific embodiments and applications thereof, numerous modifications and variations could be made thereto by those skilled in the art without departing from the scope of the invention set forth in the claims.

What is claimed is:

1. A method of testing an integrated circuit (IC) wafer comprising the steps of:

providing an IC wafer;

providing a wafer test fixture, the wafer test fixture having a base plate and a top plate;

holding the wafer between the base plate and top plate;

sealably attaching the wafer to the base plate so as to form a first cavity underneath the wafer;

sealably attaching the wafer to the top plate so as to form a second cavity above the wafer;

pressurizing the first cavity to stress the wafer;

measuring the pressure in the pressurized cavity; and measuring the deflection of the integrated circuit wafer from the pressurized cavity.

* * * * *